United States Patent
Xiong et al.

(10) Patent No.: US 9,928,592 B2
(45) Date of Patent: Mar. 27, 2018

(54) IMAGE-BASED SIGNAL DETECTION FOR OBJECT METROLOGY

(71) Applicant: Sensors Unlimited, Inc., Princeton, NJ (US)

(72) Inventors: Ziyou Xiong, Wethersfield, CT (US); Alan M. Finn, Hebron, CT (US)

(73) Assignee: Sensors Unlimited, Inc., Princeton, NJ (US)

(*) Notice: Subject to any disclaimer, the term of this patent is extended or adjusted under 35 U.S.C. 154(b) by 39 days.

(21) Appl. No.: 15/069,610

(22) Filed: Mar. 14, 2016

(65) Prior Publication Data
US 2017/0262986 A1    Sep. 14, 2017

(51) Int. Cl.
*G06K 9/00*    (2006.01)
*G06T 7/00*    (2017.01)

(52) U.S. Cl.
CPC .......... *G06T 7/0014* (2013.01); *G06T 7/0024* (2013.01); *G06T 7/0057* (2013.01);
(Continued)

(58) Field of Classification Search
CPC ......... A61B 1/00186; A61B 1/06; A61B 5/00; A61B 5/0013; A61B 5/0015; A61B 5/0022; A61B 5/0033; A61B 5/0035; A61B 5/0037; A61B 5/0048; A61B 5/0053; A61B 5/0059; A61B 5/0064; A61B 5/0077; A61B 5/0082; A61B 5/0086; A61B 5/103; A61B 5/1032; A61B 5/107–5/1072; A61B 5/1077; A61B 5/150068; A61B 5/411; A61B 5/44–5/445; A61B 5/6842; A61B 5/685; A61B 8/0858; A61B 10/0035; A61B 2018/00458; A61B 2018/0047;
(Continued)

(56) References Cited

U.S. PATENT DOCUMENTS 6,081,612 A    6/2000   Gutkowicz-Krusin et al.
6,381,026 B1   4/2002   Schiff et al.
(Continued)

FOREIGN PATENT DOCUMENTS

CA    2828785 A1       9/2012
WO    WO-01026050 A2   4/2001
(Continued)

OTHER PUBLICATIONS

Rosen et al., "On in-vivo skin topography and replication techniques", 2005, Journal of Physics : Conference Series 13, 7th International Symposium on Measurement Techonology and Intelligent Instruments, pp. 325-329.*
(Continued)

*Primary Examiner* — Jose Couso
(74) *Attorney, Agent, or Firm* — Locke Lord LLP; Scott D. Wofsy; Joshua L. Jones

(57) ABSTRACT

A method of image-based quantification for allergen skin reaction includes imaging an area of skin that has been subject to a skin-prick test to produce one or more images of the area. The method includes identifying regions of wheal and/or flare in the one or more images of the area and quantifying weal and/or flare indicators based on the regions identified. The method also includes outputting results of the quantified wheal and/or flare indicators indicative of quantified allergen skin reaction.

16 Claims, 11 Drawing Sheets

(52) U.S. Cl.
CPC ............... *G06T 2207/30088* (2013.01); *G06T 2207/30244* (2013.01)

(58) Field of Classification Search
CPC .......... A61B 2090/395; A61B 2503/12; A61B 2560/0242; G06T 5/50; G06T 7/0012; G06T 7/0014; G06T 2207/20212; G06T 2207/20216; G06T 2207/20221; G06T 2207/20224; G06T 2207/30004; G06T 2207/30088; G06T 2207/30096; G06T 2207/30244; G06T 7/254; G06F 19/30; G06F 19/34; G06F 19/3406; G06F 19/3443; G06F 19/345; G06K 9/00496; G06K 9/62; G06K 9/78; G09G 2340/10; G09G 2340/12; G09G 2380/08; A61M 37/0015; A61M 2037/0023; A61M 2037/0046; A61M 2037/0053; A61M 2037/0061
See application file for complete search history.

(56) References Cited

U.S. PATENT DOCUMENTS

| | | | |
|---|---|---|---|
| 6,400,831 | B2 | 6/2002 | Lee et al. |
| 6,707,851 | B1 | 3/2004 | Choi et al. |
| 6,993,167 | B1* | 1/2006 | Skladnev ............... A61B 5/444 382/128 |
| 7,245,766 | B2 | 7/2007 | Brown et al. |
| 7,430,320 | B2 | 9/2008 | Lee et al. |
| 7,469,060 | B2 | 12/2008 | Bazakos et al. |
| 7,841,533 | B2 | 11/2010 | Kotlarsky et al. |
| 7,942,827 | B2 | 5/2011 | Mir et al. |
| 8,270,695 | B2 | 9/2012 | Luo et al. |
| 8,284,194 | B2 | 10/2012 | Zhang et al. |
| 8,457,372 | B2 | 6/2013 | Fu et al. |
| 8,682,097 | B2* | 3/2014 | Steinberg ................. G06T 5/50 382/275 |
| 8,755,597 | B1 | 6/2014 | Tantalo et al. |
| 8,891,820 | B2 | 11/2014 | Owechko et al. |
| 9,036,888 | B2 | 5/2015 | Kamath et al. |
| 9,061,109 | B2 | 6/2015 | Wood et al. |
| 9,087,372 | B2 | 7/2015 | Dekel |
| 9,198,640 | B2 | 12/2015 | Arieli et al. |
| 9,224,205 | B2 | 12/2015 | Tsin et al. |
| 2002/0173723 | A1 | 11/2002 | Lewis et al. |
| 2007/0125390 | A1* | 6/2007 | Afriat ..................... A61B 5/442 128/898 |
| 2009/0136102 | A1* | 5/2009 | Kimpe ..................... G06T 5/50 382/128 |
| 2011/0199335 | A1 | 8/2011 | Li et al. |
| 2012/0253224 | A1* | 10/2012 | Mir ......................... A61B 5/441 600/556 |
| 2013/0137961 | A1* | 5/2013 | Barnes ................. A61B 5/0062 600/407 |
| 2014/0010423 | A1 | 1/2014 | Soldatitsch et al. |
| 2014/0022281 | A1 | 1/2014 | Georgeson et al. |
| 2014/0206443 | A1 | 7/2014 | Sharp et al. |
| 2014/0313294 | A1 | 10/2014 | Hoffman |
| 2014/0368639 | A1 | 12/2014 | Wu et al. |
| 2015/0005644 | A1 | 1/2015 | Rhoads |
| 2015/0025412 | A1 | 1/2015 | Gillman et al. |
| 2015/0138342 | A1 | 5/2015 | Brdar et al. |
| 2015/0294476 | A1 | 10/2015 | Tang et al. |
| 2015/0297129 | A1 | 10/2015 | Gilbert |
| 2016/0058288 | A1* | 3/2016 | DeBernardis ........ A61B 5/0077 600/477 |
| 2016/0093099 | A1* | 3/2016 | Bridges .............. G06K 9/00201 348/50 |
| 2017/0245792 | A1* | 8/2017 | Tversky ................. A61B 5/411 |
| 2017/0258391 | A1* | 9/2017 | Finn ....................... A61B 5/411 |
| 2017/0262965 | A1* | 9/2017 | Xiong ..................... G06T 5/003 |
| 2017/0262977 | A1* | 9/2017 | Finn ....................... G06T 7/0012 |
| 2017/0262979 | A1* | 9/2017 | Xiong ................... G06T 7/0012 |
| 2017/0262985 | A1* | 9/2017 | Finn ..................... G06T 7/0014 |

FOREIGN PATENT DOCUMENTS

| | | |
|---|---|---|
| WO | WO-2013160780 A1 | 10/2013 |
| WO | WO-2014011182 A1 | 1/2014 |
| WO | WO-2014140215 A1 | 9/2014 |
| WO | WO-2014182932 A1 | 11/2014 |

OTHER PUBLICATIONS

Zahouani et al., "Contribution of human skin topography to the characterization of dynamic skin tension during senescence : morpho-mechanical approach", 2014, Journal of Physics : Conference Series 483, 14th International Conference on Metrology and Porperties of Engineering Surfaces, pp. 1-15.*
Svelto et al., "Semi-and-Automatic Wheal Measurement System for Prick Test Digital Imaging and Analysis", Oct. 4-6, 2016, IEEE Conference on Imaging Systems and Techniques (IST), pp. 1-5.*
Bulan, O., "Improved Wheal Detection from Skin Prick Test Images", Proc. of SPIE9024, Image Processing :Machine Vision Applicaitons VII, 90240J, pp. 1-10, Mar. 7, 2014.*
Suchecki, R. et al., "Quantitative results estimation of allergological skin prick test using computer planimetry", Institure of Electronic System, Warsaw University of Technology, Poland, pp. 1-5, 2006.*
MacGlashan d., et al., "Skin Test Reading Device and Associated Systems and Methods".
Bulan, O., "Improved Wheal Detection from Skin Prick Test Images", Proc. SPIE9024, image Processing: machine Vision Applications VII, 90240J, Mar. 7, 2014.
Dos Santos, R.V. et al., "Beyond Flat weals [sic]: validation of a three-dimensional imaging technology that will improve skin allergy research", Clinical and Experimental Dermatology, 33, 772-775, 2008.
Stamatas, G.N., et al., "In vivo monitoring of cutaneous edema using spectral imaging in the visible and near infrared", J. invest. Dermatol. Aug; 126(80: 1753-60, 2006.
"FLARE Diagnostics is a leader in the development and production of medical imaging devices used to evaluate allergic and dermatological conditions." Flare Dignostics.com Powered by Squarespace. 2016. http://www.flarediagnostics.com/index/.
Sören Jaspers and Christian Benderoth; PRIMOS 3D Digital Frame Projection. E. Berardesca et al. (eds.), non Invasive Diagnostic Techniques in Clinical Dermatology, DOI 10.1007/978-3-642-32109-2_4, © Springer Berlin Heidelberg 2014.
X. Justo, I. Diaz, J.J. Gil & G. Gastaminza. Prick Test: Evolution towards automated reading. Allergy: European Journal of Allergy and Clinical Immunology. Apr. 19, 2016.

* cited by examiner

IMAGE-BASED SIGNAL DETECTION FOR OBJECT METROLOGY

BACKGROUND OF THE INVENTION

1. Field of the Invention

The present disclosure relates to imaging, and more particularly to imaging such as used in image based quantification of allergen skin reaction.

2. Description of Related Art

Manual measurement of skin wheal size is the dominant method to determine allergen reaction in skin-prick tests, although other manual or semi-automated measurement processes are known. For example, one technique is to transfer a drawn outline to paper for scanning and measurement. These manual methods are cumbersome, error prone, and introduce an undesirable degree of variability between practitioners.

While some image-based techniques have been suggested as improvements over manual measurement processes, these image-based techniques are usually based on comparison with predefined or ad hoc pixel intensity thresholds. Thus these image-based techniques are subject to error when imaging conditions deviate from the conditions used to set the thresholds. Such conditions include lighting, subject-to-subject differences, or when the area imaged has similar pixel values to those in its surroundings.

Such conventional methods and systems have generally been considered satisfactory for their intended purpose. However, there is still a need in the art for improved imaging techniques. The present disclosure provides a solution for this need.

SUMMARY OF THE INVENTION

A method of image-based signal detection for correction for images of allergen skin reaction includes obtaining a first image of an area of skin that has been subjected to a skin prick-test, obtaining a second image of the area of skin, and projecting a metrology signal onto the area of skin during obtaining of at least one of the first and second images so that the first and second images differ with respect to presence of the metrology pattern. The method includes registering the first and second images to form a registered pair of images and performing a subtraction operation on the registered pair of images to obtain an image of the metrology pattern wherein the metrology pattern is isolated from its surroundings. An image of area of skin is rectified using the image of the metrology pattern isolated from its surroundings for quantification of wheal and/or flare objects in the image rectified. The registration may be achieved by feature detection, such as SIFT, SURF, ASIFT, other SIFT variants, a Harris Corner Detector, SUSAN, FAST, a Phase Correlation, a Normalized Cross-Correlation, GLOH, BRIEF, CenSure/STAR, ORB, or the like, and a random sample consensus (RANSAC) such as MSAC, MLESAC, Guided-MLESAC, PROSAC, KALMANSAC, and/or any other suitable technique. The method includes outputting data indicative of the quantified wheal and/or flare objects.

Rectifying the image of the area of skin can include correcting for camera pose to be as if the image were formed from an imaging device viewing the area of skin perpendicularly. Rectifying the image of the area of skin can include correcting for camera range to be as if the image were formed a predetermined distance from the area of skin. Rectifying an image can include rectification performed on image that does not include the metrology pattern.

Obtaining the first and second images and projecting the metrology signal can include obtaining one of the first and second images with the metrology signal projected, and obtaining the other of the first and second images with the metrology signal not projected. It is also contemplated that projecting the metrology signal can include projecting the metrology signal with intensity that varies with time so the intensity of the metrology signal in the first and second images is different. The method can include modeling the metrology signal and using the modeled metrology signal to subtract the metrology signal from the first and second images. Obtaining the first and second images can include obtaining both from a single imaging device. Obtaining the first and second images can include obtaining the images on at least one of a sensor for visible light, a sensor for a non-visible portion of electromagnetic spectrum, or a three-dimensional sensor, and wherein projecting the metrology pattern includes projecting a metrology pattern detectable using the sensor.

Projecting a metrology signal onto the area of skin can include projecting a plurality of laser dots onto the area of the skin. It is also contemplated that projecting the metrology signal can include projecting a metrology signal having a single source including at least one of a predetermined shape that deforms under change in pose and distance, or is detected at a sensor separate from the projector, for example. More generally, the projected metrology signal may also allow determination of the three-dimensional shape of the skin area as with the use of depth sensing, e.g., a structured light measurement, a phase shift measurement, a time of flight measurement, or the like. It is further contemplated that projecting the metrology signal can include projecting a metrology signal having a single laser dot, wherein rectifying an image includes range finding based on apparent size of the laser dot in the image of the metrology pattern wherein the metrology pattern is isolated from its surroundings.

A system for image correction for images of allergen skin reaction includes an imaging device including a projecting device, an output device, and a module operatively connected to the imaging device and the output device. The module is configured to execute machine readable instructions to perform any embodiment or combination of embodiments disclosed herein. The imaging device can include at least one of a sensor for visible light, a sensor for a non-visible portion of electromagnetic spectrum, or a three-dimensional sensor. The projecting device can be configured to project a metrology pattern detectable using the sensor.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1A:
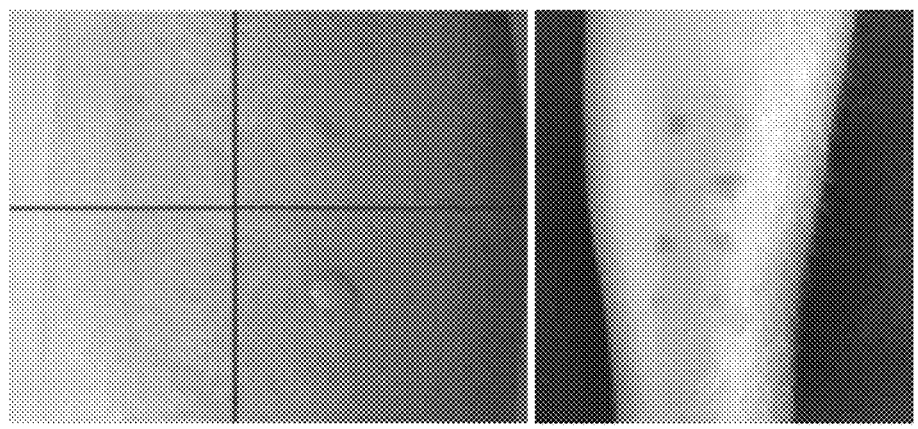
FIG. 1A is a side by side comparison of an image in the visible spectrum of an area of skin that has been subject to a skin-prick test on the left, and on the right an image in the infrared of an area that has similarly been subject to a skin-prick test.

Reference will now be made to the drawings wherein like reference numerals identify similar structural features or aspects of the subject disclosure. For purposes of explanation and illustration, and not limitation, a partial view of an exemplary embodiment of a method in accordance with the disclosure is shown in FIG. 1B and is designated generally by reference character 100. Other embodiments of methods in accordance with the disclosure, or aspects thereof, are provided in FIGS. 1A, 1C and 2-6B, as will be described. The systems and methods described herein can be used to provide for more accurate, consistent, convenient, and diagnostically significant measurement systems and methods for allergen skin reaction quantification.

With the image-based quantification disclosed below, skin-prick allergen testing may be synergistically designed for improved performance of the image-based quantification. That is, the injected allergen may additionally include non-allergic, non-toxic materials, compounds, or biologicals that preferentially disperse through the edema of an allergic reaction and are more easily, reliably, and quantifiably detectable by automated means. In particular, there are now thousands of protein and non-protein organic fluorophores with a Stokes (or Anti-Stokes) frequency shifting property. These are used extensively as dyes to stain biological specimens for fluorescence microscopy. Also, very recently, physicists and materials scientists have developed microstructures called Quantum Dots that have similar or better frequency shifting properties. In addition to the allergen, a small quantity of a fluorophore or Quantum Dots may be deposited by the skin prick device and they may preferentially disperse through the edema to provide an easily detectable, unique fluorescent response for reliable, accurate, repeatable wheal quantification by image-based quantification designed for the fluorescence. The unique fluorescent response may be, for instance, a color anywhere in the electromagnetic spectrum where the sensors are sensitive and that does not normally occur in imagery from the sensors. This unique response may be evinced by excitation illumination which may be pulsed on and off to provide differential imagery for subsequent processing. These techniques can be part of the receiving imagery 102 operation described below, e.g., as preparatory procedures.

Figure 1B:
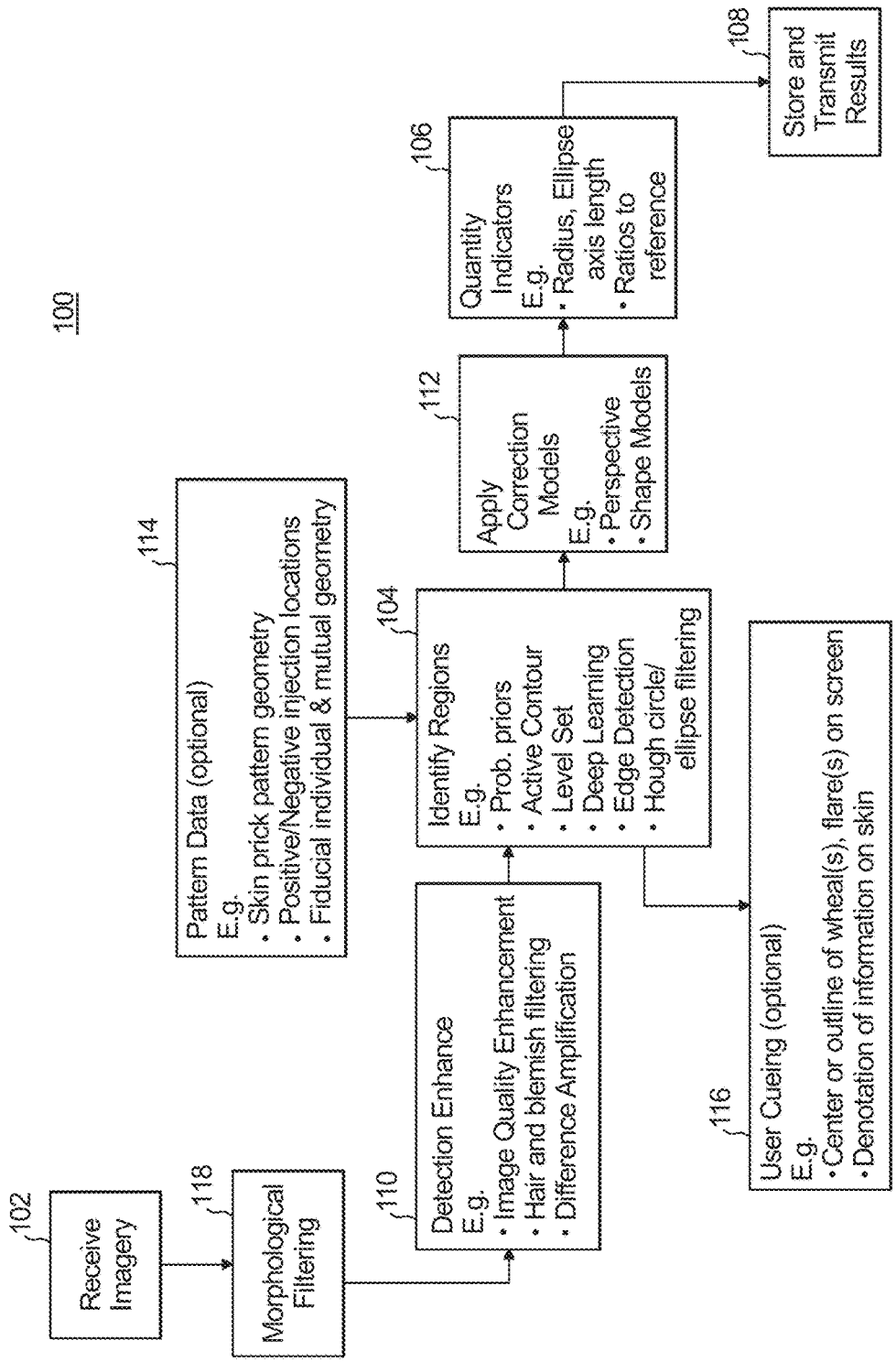
FIG. 1B is a schematic view of an exemplary embodiment of a method in accordance with this disclosure.

With reference first to FIG. 1A, in the image on the left in FIG. 1A, an image of skin is shown wherein the image was taken in the visible spectrum. The presence of some wheal and/or flare objects in the image are visible, the results of the skin being subject to a skin-prick test. Both reaction and non-reaction sites are included in the image. The image on the right in FIG. 1A is an infrared image of an area of skin with wheal and/or flare objects showing, also the result of a skin-prick test. Comparing these two images demonstrates that for certain reaction characteristics, it is easier to see and detect wheal and/or flare objects in infrared images than in visible spectrum images. Examples of these characteristics are morphology, intensity, intensity variation, and texture. Other characteristics such as fluorescence may be more easily detected or observed in visible spectrum images with or without background filtering.

Referring now to FIG. 1B, a method 100 of image-based quantification for allergen skin reaction includes imaging an area of skin that has been subject to a skin-prick test to produce one or more images of the area, and the imagery is received for quantification as denoted in FIG. 1B as receiving imagery 102. In this context an image may be a typical two-dimensional representation of the intensity recorded from a scene, but may also be a depth map, i.e., a two dimensional representation of the range to objects in the scene, although 'image' and 'depth map' are typically not synonymous. A depth map is also sometimes called a point cloud or is represented as an occupancy grid. A depth map may be sensed by a structured light measurement, phase shift measurement, time of flight measurement, stereo triangulation device, light field camera, coded aperture camera, computational imaging technique camera (structure from motion, simultaneous localization and mapping, depth from defocus, or the like), imaging radar, imaging sonar, scanning LIDAR, flash LIDAR, or like technologies.

The method 100 includes identifying 104 regions of wheal and/or flare in the one or more images and quantifying 106 weal and/or flare indicators based on the regions identified. The method 100 also includes outputting, storing, or transmitting 108 results of the quantified wheal and/or flare indicators indicative of quantified allergen skin reaction. All of the one or more images can be two-dimensional images, and identifying 104 regions and quantifying wheal and/or flare indicators can be performed on two-dimensional images without forming any three-dimensional images.

Regions of wheal and/or flare can be identified 104 and quantified 106 without requiring presence of both wheal and flare in any given region. In other words, method 100 allows for identification and quantification of flare without wheal and vice versa. Identifying 104 regions of wheal and/or flare, e.g., image segmentation, can be performed agnostically with respect to the anatomical location of the area of skin being imaged, so wheal and/or flare indicators are quantified 106 without respect to the anatomical location of the area of skin being imaged. This allows for flexibility in the anatomical site of the skin-prick test, so, for example method 100 can utilize images of forearm skin-prick tests, or skin-prick tests on a subject's back. Similarly, identifying 104 regions of wheal and/or flare can be performed agnostically with respect to the relative position of the imaging device and the area of skin being imaged, so wheal and/or flare indicators are quantified 106 without respect to the relative position of the imaging device and the area of skin being imaged. This allows for considerable flexibility in positioning the area of skin relative to the imaging device during imaging, so for example in a forearm skin-prick test, it is not necessary to constrain the subject's forearm to a precise location within the imaging device's field of view. Regions of wheal and/or flare can be identified 104 without predefined or ad hoc pixel intensity thresholds, e.g., by statistical automatic threshold determination using methods such as Otsu's Method, Valley Emphasis Method, FireFly Method, Fireworks Method, Multilevel Methods, Optimization-Based Methods (e.g., particle swarm optimization, honey bee mating), and/or any other suitable method. Regions of wheal and/or flare can be additionally identified 104 by color in the case of fluorescence.

After imaging the area of skin and before identifying 104 regions of wheal and/or flare, morphological filtering 118 may be applied for hair and blemish removal, vein removal, noise removal, or the like. Morphological filtering 118 includes identifying and removing portions of the one or more images based on one or more shapes detected in the one or more images. A shape is identified by shape features (descriptors) which may be computed by Histogram of Oriented Gradients (HoG), Zernike Moments, Centroid Invariance to boundary point distribution, contour curvature, and like techniques. Other features may be extracted to provide additional information for morphological filtering. Examples of other features include, but are not limited to, a Scale Invariant Feature Transform (SIFT), Speed-Up Robust Feature (SURF) algorithm, Affine Scale Invariant Feature Transform (ASIFT), other SIFT variants, a Harris Corner Detector, a Smallest Univalue Segment Assimilating Nucleus (SUSAN) algorithm, a Features from Accelerated Segment Test (FAST) corner detector, a Phase Correlation, a Normalized Cross-Correlation, a Gradient Location Orientation Histogram (GLOH) algorithm, a Binary Robust Independent Elementary Features (BRIEF) algorithm, a Center Surround Extremas (CenSure/STAR) algorithm, and an Oriented and Rotated BRIEF (ORB) algorithm. The shape features are classified as a shape to be removed by classification based on the features using techniques such as clustering, Deep Learning, Convolutional Neural Network, Support Vector Machine (SVM), Decision Trees, Fuzzy Logic, and the like. Veins in the image may be removed by morphological filtering 118, but preferably after difference amplification (Eulerian Video Magnification) or like techniques that enhance dynamics from multiple images or video from different respective bands and/or modalities. The removal of identified shapes may be by simply overwriting the shape with some constant value or may be done by in-painting After imaging and filtering the area of skin at least one of the one or more images can be enhanced 110 to facilitate identification of regions of wheal and/or flare. Enhancing 110 can include at least one of background subtraction, normalization, histogram equalization, adaptive histogram equalization, contrast limited adaptive histogram equalization (CLAHE), edge enhancement, Weiner Filtering Blind Deconvolution, or like techniques. Background subtraction may include subtraction of an image taken before the skin prick test where the prior image is registered to and subtracted from the image after the skin prick test. This background subtraction produces differential imagery where the change due to the allergen reaction is substantially isolated from the rest of the imagery. This method may also be particularly useful in removing visibly obscuring features such as a tattoo. Other enhancements can include autofocus, sharpening, unsharp masking, white balance, hue and gamma adjustment, cross polarization, and the like. Those skilled in the art will readily appreciate that any other suitable image enhancement or combination of enhancements can be used without departing from the scope of this disclosure.

Identifying 104 regions of wheal and/or flare can include utilizing 114 pattern data from a database, wherein the database includes at least one of skin prick pattern geometry, positive/negative injection locations, fiducial individual and mutual geometry, or images. It is also contemplated that identifying 104 regions of wheal and/or flare can include accepting 116 user input, or user cueing, and including the input in identifying regions of wheal and/or flare. The user input can include at least one of center and/or inline or outline of one or more wheals and/or flares on a display indicative of the one or more images, or denoting of information on the skin. In this context, inline is the opposite of outline, i.e., denoting the interior of a shape.

Identifying 104 regions of wheal and/or flare can include at least one of applying probabilistic priors based on at least one of a priori pattern data or user cueing, active contour, level set segmentation, deep learning based on trained segmentation operators, edge detection using optimal thresholding, Hough circle or ellipse fitting, or the like.

The method 100 can include applying 112 one or more correction models to the one or more images before or after identifying 104 regions of wheal and/or flare and before quantifying wheal and/or flare indicators. Applying 112 one or more correction models can include at least one of applying a perspective model or applying a shape model.

Quantifying 106 wheal and/or flare indicators can include at least one of quantifying area, absolute radius, absolute ellipse axis length, or ratios of radius or ellipse axis length compared to a reference. Quantifying 106 can include computing statistical values such as area by integrating an active contour or radius or largest diameter from a circle or ellipse fit. The statistics can include relative sizes compared to reference regions or may be in absolute units based on a calibration and/or an optional correction for perspective or shape operation.

Figure 1C:
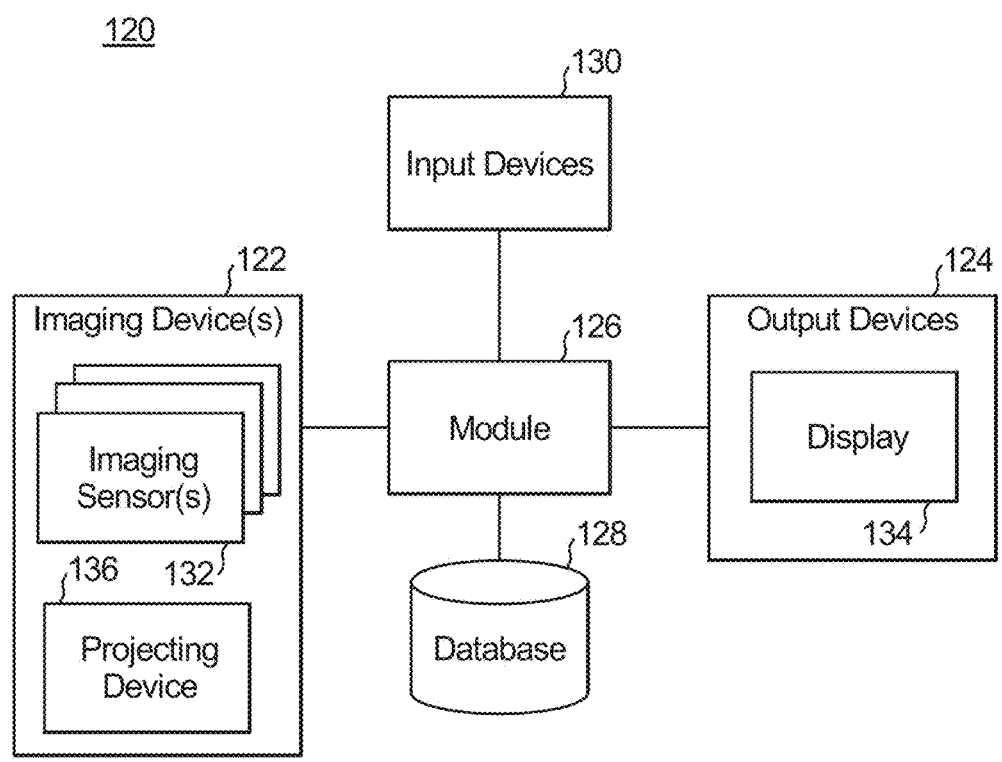
FIG. 1C is a schematic view of an exemplary embodiment of a system for implementing methods disclosed herein.

With reference now to FIG. 1C, a system 120 for image-based quantification for allergen skin reaction includes an imaging device 122, at least one output device 124, and a module 126 operatively connected to the imaging device 122 and output device 124. The module 126 is configured to execute machine readable instructions to perform any embodiment or combination of the methods described above. The imaging device 122 may contain one or more imaging sensors 132 and may contain a projecting device 136. Imaging sensors 132 may be sensitive to any portion of the electromagnetic or acoustic spectrum, but can advantageously include one imaging sensor sensitive to the visible spectrum and one sensor sensitive to the near infrared spectrum. Projecting device 136 optionally provides illumination, and/or projects fiducial marks, and/or projects imagery useful in pose and range estimation, in a segment of the electromagnetic spectrum that may overlap, at least in part, the sensitive spectrum of imaging device 122. The illumination provided by projecting device 136 may be automatically adapted by module 126 or may be controlled by a user through input device 130. Similarly, any polarization of radiation from projecting device 136 and polarization of radiation received by sensors 132 may be automatically adapted by module 126 or may be controlled by a user through input device 130. The automatic adaptation may be achieved by automatically varying the illumination and/or polarization to optimize one or more image quality metrics.

The system 120 can include a database 128 operatively connected to the module 126, wherein the database 128 includes at least one of skin prick pattern geometry, positive/negative injection locations, fiducial individual and mutual geometry, or images wherein the module 126 is configured to execute machine readable instructions to identify regions of wheal and/or flare utilizing data from the database 128. It is also contemplated that an input device 130 can be operatively connected to the module 126, wherein the input device 130 is configured to receive user input, and wherein the module 126 is configured to execute machine readable instructions to identify regions of wheal and/or flare by accepting user input and including the input in identifying regions of wheal and/or flare.

Figure 2:
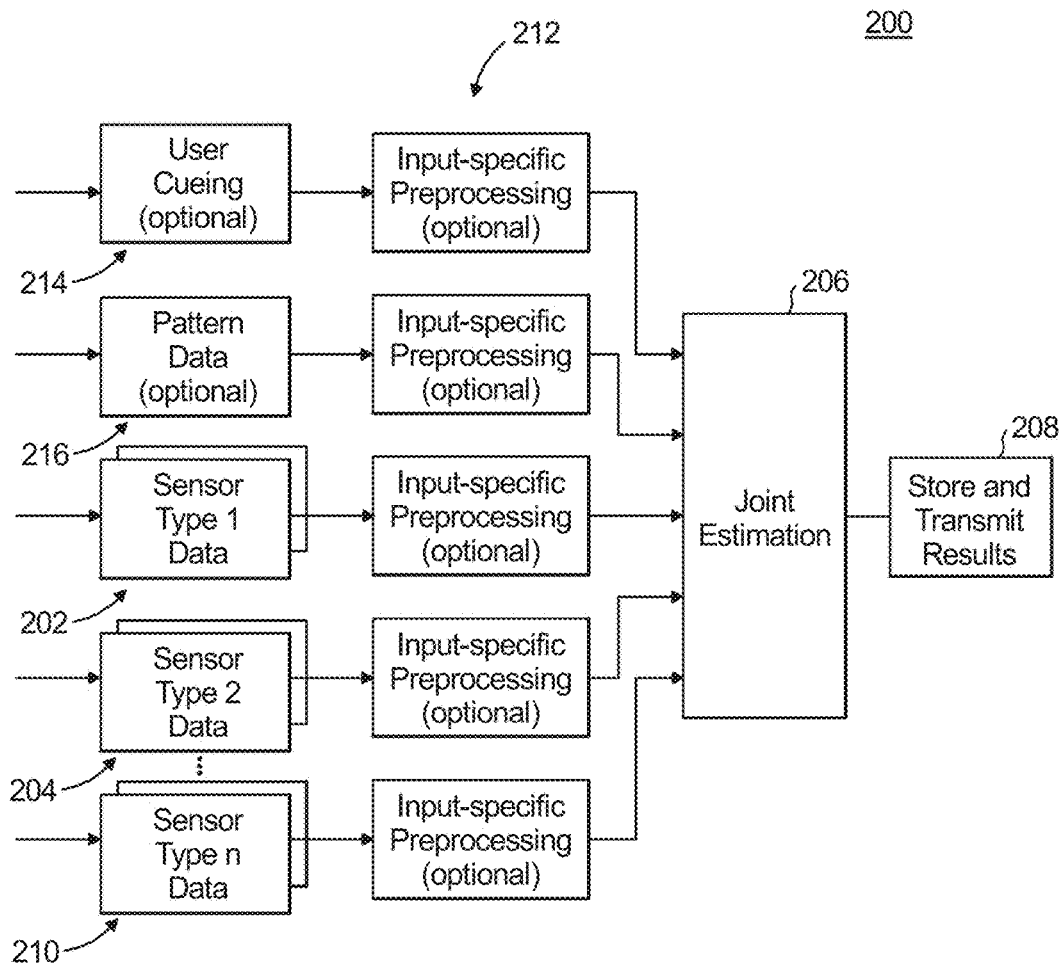
FIG. 2 is a schematic view of an exemplary embodiment of a method in accordance with this disclosure.

Referring now to FIG. 2, a method 200 of object detection for allergen skin reaction testing includes receiving 202 sensor data of a first modality pertaining to skin that has been subject to a skin-prick test. The method 200 also includes receiving 204 sensor data of a second modality pertaining to the skin that has been subject to a skin-prick test. The sensor data is used from both the first and second modalities in joint estimation 206 to locate at least one wheal and/or flare object indicative of quantified allergen skin reaction. The method 200 also includes outputting or transmitting 208 results including parameters and/or statistics of identified wheal and/or flare objects. Transmitting 208 can include transmitting for eventual storage, display, subsequent processing, or the like. Additional sensor data from one or more other modalities can be received and used in joint estimation 206, as indicated in FIG. 2 by the ellipses and reference character 210.

After receiving 202/204/210 the sensor data and before using the sensor data in joint estimation 206, input-specific preprocessing 212 can be performed on any or all of the sensor data. Performing input-specific preprocessing 212 can include converting at least some of the sensor data of the first and second modalities into respective spatial probability density functions of spatial location of wheal and/or flare objects. Performing input-specific preprocessing may also include incorporation of expected interrelationships within and between each of the first and second modalities respectively. The incorporation may include a priori known information, e.g., from database 128. For example, such an interrelationship can include the approximately concentric relationship of a wheal and a flare. Input-specific preprocessing 212 can include mosaicking to create a larger image depending on the field of view of the sensor 202/204/210. The mosaicking may be by any suitable technique and may utilize natural features in the image or may utilize fiducial marks.

As part of joint estimation 206, sensor data may be spatially registered to establish a common coordinate system. This can advantageously be achieved by feature detection, such as SIFT, SURF, ASIFT, other SIFT variants, a Harris Corner Detector, SUSAN, FAST, a Phase Correlation, a Normalized Cross-Correlation, GLOH, BRIEF, CenSure/STAR, ORB, or the like, and a random sample consensus (RANSAC) such as MSAC, MLESAC, Guided-MLESAC, PROSAC, KALMANSAC, and/or any other suitable technique. Joint estimation 206 can include Bayesian estimation using the spatial probability density functions. It is also contemplated that joint estimation 206 can include employing at least one of maximum likelihood (ML), maximum a priori (MAP), or non-linear least squares (NNLS).

In another aspect, joint estimation 206 can include utilizing one or more thresholds in the detection of wheal and/or flare objects. The one or more thresholds can be fixed a priori. It is also contemplated that the one or more thresholds can be chosen, e.g., automatically, with respect to desired detection tradeoffs between missed detection and false alarm using criteria including at least one of equal error rate (EER) or constant false alarm rate (CFAR). Thresholds can also be computed from the data, e.g., by using methods such as Otsu's Method, Valley Emphasis Method, FireFly Method, Fireworks Method, Multilevel Methods, Optimization-Based Methods (e.g., particle swarm optimization), and/or any other suitable method. Joint estimation 206 can provide results including at least one of parameters or statistics of detected wheal and/or flare objects, wherein the parameters include at least one of location, boundaries, areas, or uncertainties.

The sensor data of the first modality and the sensor data of the second modality can be received from two separate respective two-dimensional imaging sensors, e.g., imaging sensors 132 in FIG. 1C. The first and second modalities can differ from one another spectrally. For example a first one of the sensors 132 can be a visible spectrum sensor, and the other can be a infrared sensor. The data of the first and second modalities can be received from a single two-dimensional imaging sensor at two different times. The first and second modalities can include at least one of acoustic or three-dimensional imagery including at least one of structured light measurements, phase shift measurements, time of flight measurements, stereo triangulation measurements, sheet of light triangulation measurements, light field measurements, coded aperture measurements, computational imaging technique measurements, imaging radar measurements, imaging sonar measurements, scanning LIDAR measurements, flash LIDAR measurements, passive Infrared (PID) measurements, small focal plane array (FPA) measurements, or any other suitable modality or a combination of the foregoing.

The method 200 can include receiving non-sensor data including at least one of user cueing input 214 or a priori known pattern data 216 including at least one of geometry of a skin-prick device, relative location of reference skin-pricks, or relative location or metric size of fiducial marks. User cueing input 214 and known pattern data 216 can optionally be preprocessed 212 as described above with respect to sensor data.

With reference to FIG. 1C, system 120 for object detection in allergen skin reaction testing includes an imaging device 122 with at least one sensor 132, at least one output device 124, and a module 126 operatively connected to the imaging device 122 and output device 124. The module 126 is configured to execute machine readable instructions to perform any embodiment or combination of embodiments of methods disclosed herein. The imaging device 122 may contain one or more imaging sensors 132 and may contain a projecting device 136. Imaging sensors 132 may be sensitive to any portion of the electromagnetic spectrum or acoustic spectrum, but can advantageously include one imaging sensor sensitive to the visible spectrum and one sensor sensitive to the near infrared spectrum. Projecting device 136 optionally provides illumination and/or projects fiducial marks in a segment of the electromagnetic spectrum that may overlap, at least in part, the sensitive spectrum of imaging device 122. The system 120 can include a database 128 operatively connected to the module 126, wherein the database 128 includes a priori known pattern data including at least one of geometry of a skin-prick device, relative location of reference skin-pricks, or relative location or metric size of fiducial marks, wherein the module 126 is configured to execute machine readable instructions to identify regions of wheal and/or flare utilizing pattern data from a database 128. It is also contemplated that the system 120 can include an input device 130 operatively connected to the module 126, wherein the input device 130 is configured to receive user input, and wherein the module 126 is configured to execute machine readable instructions to identify regions of wheal and/or flare by accepting user cueing input and including the user cueing input in the joint estimation.

Figure 3:
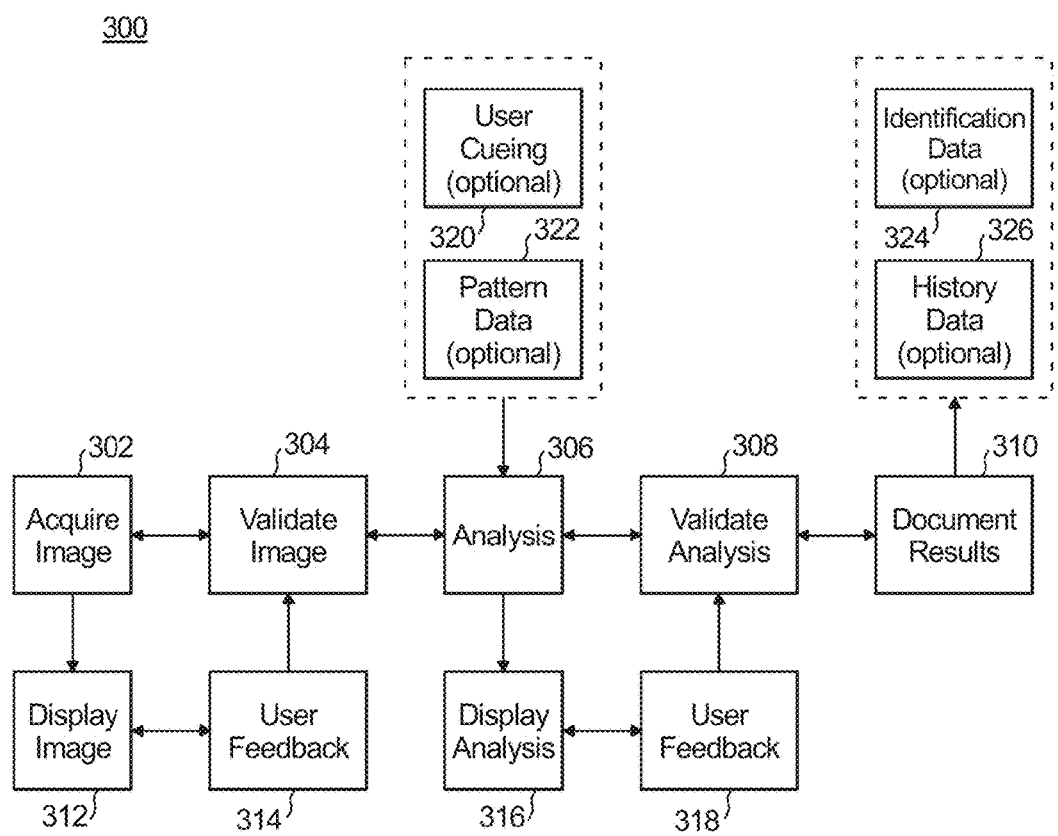
FIG. 3 is a schematic view of an exemplary embodiment of a method in accordance with this disclosure.

With reference now to FIG. 3, a method 300 of quantification for allergen skin reaction includes acquiring 302 one or more images of skin of a patient or subject that has been subject to a skin-prick test, validating 304 the one or more images for suitability for analysis, analyzing 306 the one or more images upon validation to produce results indicative of quantified allergen skin reaction, validating 308 the results, and documenting or outputting 310 the results.

Validating 304 the one or more images can include displaying 312 the one or more images and receiving 314 user input including at least one of an indication of whether a given image is valid for analysis, an indication that a given image should be reacquired, or an indication of a modification to a given image that will make the given image valid for analysis. Displaying 312 the one or more images and receiving 314 user input can be repeated iteratively as needed to validate the one or more images. Validating 304 the one or more images may also include automated validation or presenting the results of automated validation to the user and receiving 314 user input including an indication of whether the automated analysis is correct. The automated validation may include focus validation, dynamic range validation, sharpness validation, image quality metrics like DM, NQM, UQI, IFC (and its variants), NIQE, BRISQUE, DIIVINE, BLINDS, JNB, NORM, PSNR (and its variants), SSIM (and its variants) or like techniques. Focus validation may include comparison of the high frequency components of a spatial Fourier transform to a threshold. Dynamic range validation may include the difference between the maximum and minimum intensity in an image. Sharpness validation may include the mean of a gradient filter.

Validating 308 the results can include displaying 316 the results and receiving 318 user input including at least one of an indication that the analysis is accepted, an indication that the analysis is rejected, or an indication that further manual and/or automated analysis is required. Displaying 316 the results and receiving user input 318 can be repeated iteratively as needed to validate the results.

Analyzing 306 can include quantification of wheal and/or flare in the one or more images of skin. Analyzing 306 the one or more images can optionally include utilizing pattern data 322 from a database, wherein the database includes at least one of skin prick pattern geometry, positive/negative injection locations, or fiducial individual and mutual geometry. Analyzing 306 the one or more images can also optionally include accepting 320 user input, e.g., user cueing, and including the input in identifying regions of wheal and/or flare, wherein the user input includes at least one of center and/or outline of one or more wheals and/or flares on a display indicative of the one or more images, or denoting of information about or on the skin. Accepting 320 user input can also include patient identification, patient history, test identification, test history, and/or the like.

Outputting 310 the results can include optionally include receiving documentation input and outputting the results together with the documentation input, wherein the documentation input includes at least one of identification 324 of a particular subject of the one or more images of skin, or prior data 326 relevant to the skin-prick test including stored images. It is also contemplated that Outputting 310 the results can include at least one of updating a database of confirmed detections of allergies, updating a database of dismissed detections of allergies, or updating a combined database of confirmed and dismissed detections of allergies. Outputting 310 the results may also include updating a database with images.

While described herein in the exemplary context of using image data, those skilled in the art will readily appreciate that method 300 can be used with non-image data as well.

Referring now to FIG. 1C, system 120 includes an input device 130, an output device 124 including a display 134 for providing a user interface, and a module 126 operatively connected to the input device 130 and output device 124. The module 126 is configured to execute machine readable instructions to perform any of the method embodiments disclosed herein or combination thereof.

The input device 130 can be configured to receive user input, and the module 126 can be configured to execute machine readable instructions to use the input as described herein in conjunction with the methods. The module 126 can be configured to execute machine readable instructions to identify regions of wheal and/or flare by accepting user cueing input and including the user cueing input in an estimation that may be a joint or multimodal estimation. The system 120 can include a database 128 wherein the module 126 is configured to execute machine readable instructions to analyze the one or more images including utilizing pattern data from the database 128, wherein the database 128 includes at least one of patient identification, patient history, test identification, test history, images, skin prick pattern geometry, positive/negative injection locations, or fiducial individual and mutual geometry.

Figure 4:
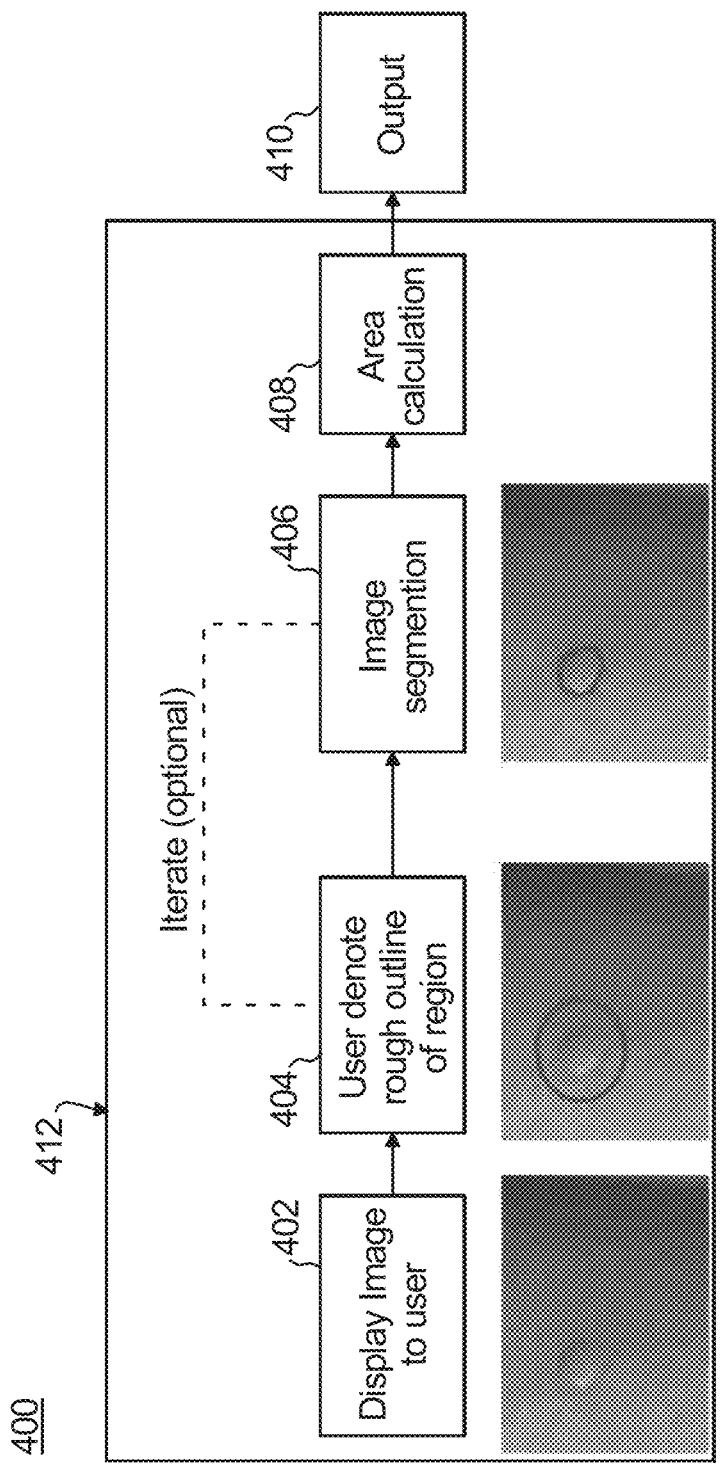
FIG. 4 is a schematic view of an exemplary embodiment of a method in accordance with this disclosure.

Referring now to FIG. 4, a method 400 for detection and metrology of allergen skin reaction includes displaying 402 an image of an area of skin that has been subject to a skin-prick test. Method 400 includes receiving 404 user input denoting an area of the image having a wheal and/or flare object, e.g., wherein the user identifies a rough outline of the region of interest. Method 400 may also include user control (e.g., through input device 130) of the imaging devices 122 including control of imaging sensors 132, e.g., to control shutter speed, ISO, exposure, focus, white balance, polarization, and/or the like, control of projecting device 136 including control of illumination, polarization, and/or control of the mode of operation of system 120 including what method of metrology will be used, which processing steps will be used, image enhancement, mosaicking, and the like. Method 400 also includes refining 406 the area denoted in the user input using automated image segmentation to identify a refined contour of the wheal and/or flare object in the image. Method 400 further includes calculating 408 quantified data such as area of the wheal and/or flare object and outputting 410 the quantified data indicative of the wheal and/or flare object based on the refined contour. Using automated image segmentation can include using at least one of an active contour, a gradient vector flow (GVF), a balloon model, a diffusion model, a geometric active contour, and/or any other suitable technique.

Method 400 includes optionally iterating 412, wherein after refining 406 the area denoted in the user input and before calculating 408 and outputting 410, the image can be displayed with an indication of the refined contour of the wheal and/or flare region, and user input can be received 404 for further refinement of the contour. Displaying the image with the refined contour and receiving 404 user input for further refinement of the contour can be iteratively repeated until an escape condition is reached. For example, the escape condition can include user input indicative of acceptability of the refined contour.

Receiving 404 user input can include receiving user input indicative of a perimeter, e.g., an external contour, enclosing the wheal and/or flare object in the image, wherein the perimeter is in the form of at least one of a circle, an oval, an ellipse, a rectangle, or a path of multiple points enclosing the object. It is also contemplated that receiving 404 user input can include receiving user input detonating an area inside the object, such as at least one of an interior point denoting the area inside the object or a series of points denoting the area inside the object. Refining 406 the area can include shrinking the external contour or expanding the interior point or points to encompass the object.

Referring to FIG. 1C, system 120 for detection and metrology of allergen skin reaction includes a display 134, an input device 130, and a module 126 operatively connected to the display 134 and input device 130. The module 126 is configured to execute machine readable instructions to perform any embodiment or combination of embodiments of methods disclosed herein.

Figure 5A:
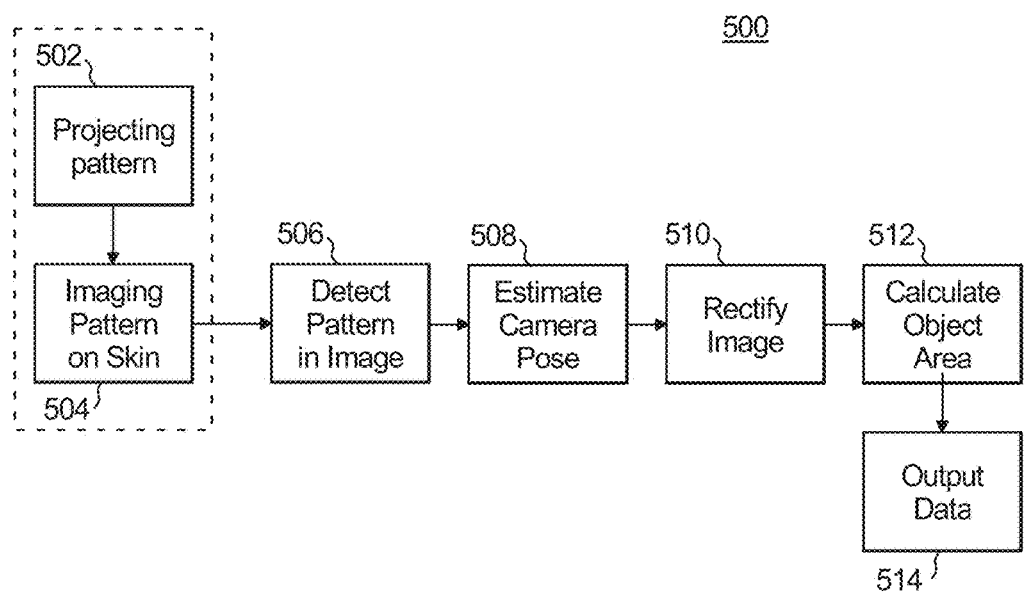
FIG. 5A is a schematic view of an exemplary embodiment of a method in accordance with this disclosure.

With reference to FIG. 5A, a method 500 of image correction for images of allergen skin reaction includes projecting 502 a pattern, e.g. a metrology pattern or signal, onto an area of skin that has been subjected to a skin-prick test. Method 500 includes imaging 504 the pattern and skin, and detecting 506 the pattern in an image that includes the pattern. The method 500 also includes estimating 508 camera pose relative to the area of skin based on the pattern detected in the image that includes the pattern. An image of the area of skin that has been subject to the skin-prick test is rectified 510 based on the camera pose estimated to be as if the image were formed from an imaging device viewing the area of skin perpendicularly and/or range corrected as if the image were formed a predetermined distance from the area of skin. The method 500 includes calculating 512 one or more areas of wheal and/or flare objects in the image rectified based on camera pose, and outputting 514 data indicative of the one or more areas calculated. It is possible to omit projecting 502 and imaging 504, e.g., if images already exist including the pattern. In other words, it is not necessary to obtain the images to practice method 500 if there already exist images that simply need to be rectified.

Projecting 502 the pattern can include projecting a plurality of laser dots from an imaging device, e.g. as discussed below with reference to FIG. 1C, wherein imaging the pattern and skin is performed using the same imaging device that projects the laser dots. The plurality of laser dots can be projected from respective lasers that are mounted parallel to one another. It is also contemplated that the lasers may have any relative orientation provided that the orientation is known, the projected dots remain in the field of view of imaging device 122, and the range is known. In this case, the detected positions of the dots may be corrected by using the range and orientation to the location they would have appeared had they been projected from lasers mounted parallel.

Figure 5B:
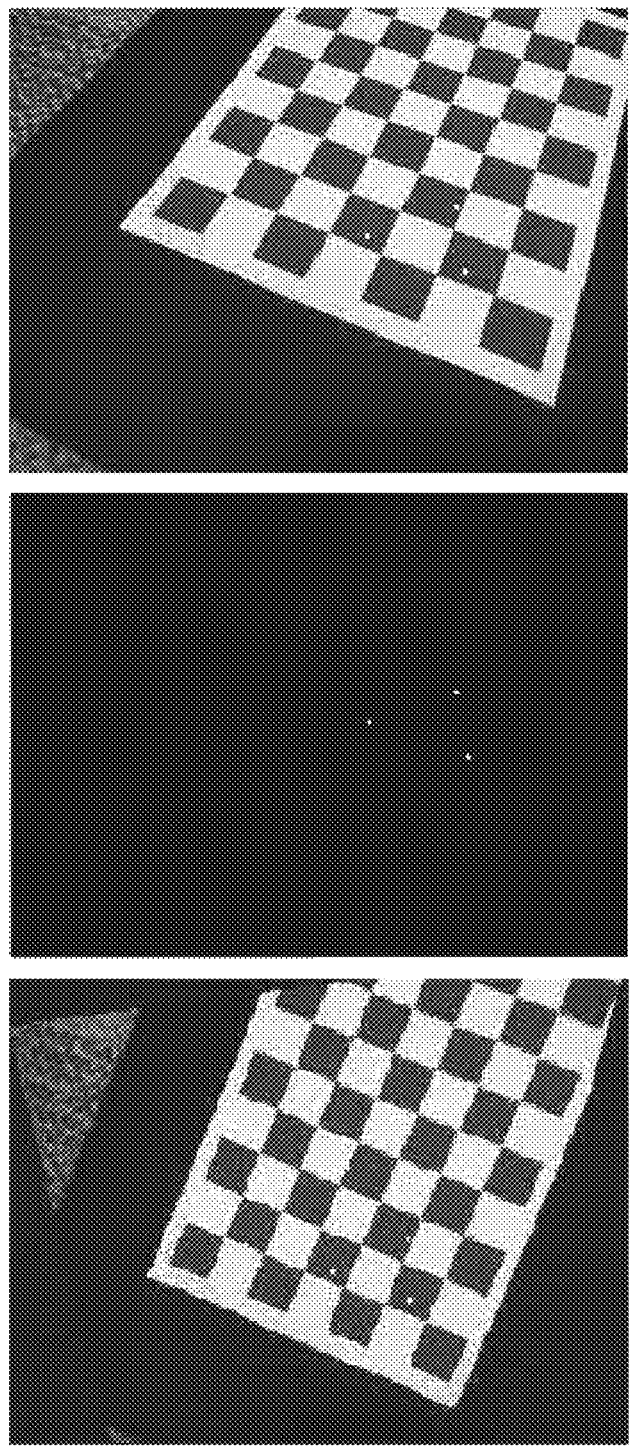
FIG. 5B is a set of images showing a) a planar object with a pattern of three laser dots projected thereon, b) an image with only the laser dots of a) showing, and c) a rectified image of the planar object, corrected for camera pose as if the image were taken perpendicular to the planar object.

An example of how method 500 can be used to rectify an image of a planar object is explained here with reference to FIG. 5B. Part a) of FIG. 5B is an image of a planar object, e.g., with a checkerboard pattern, with three laser dots projected thereon. An automatic algorithm is used to detect the three laser dots, which are shown in isolation in part b) of FIG. 5B. Part c) of FIG. 5B shows the metrically rectified checkerboard image and laser points in world coordinates. The angles between the two sides of every black or white area in the recovered checkerboard image in world coordinates are very close to ninety degrees, and the areas of the black and white squares can be calculated with reliability based on the known diameter and/or spacing of the laser dots and the apparent size/spacing in the rectified image. This technique can be applied to an area of skin subjected to a skin-prick test to accurately calculate are of wheal and/or flare objects.

Referring again to FIG. 5A, rectifying 510 the image can include modeling a non-planar anatomical surface to form a model and computing parameters of the model based on the pattern detected. The parameters of the model can be used together with the camera pose estimated to rectify the image so the area of skin in the image appears to be as if the image were formed from an imaging device viewing the area of skin perpendicularly everywhere in the area of skin subject to the skin-prick test or to calculate areas on the image as if the image were formed from an imaging device viewing the area of skin perpendicularly everywhere in the area of skin subject to the skin-prick test. The model can be n-dimensional, and wherein projecting the pattern includes projecting at least n+1 laser dots from an imaging device.

Figure 5C:
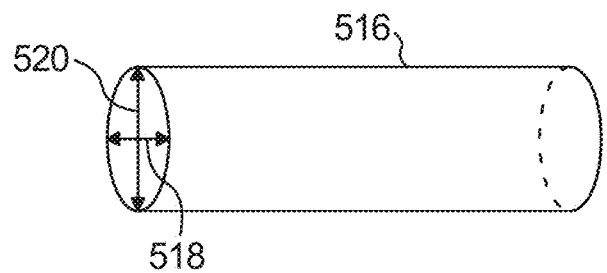
FIGS. 5C, 5D, and 5E, are perspective schematic views of three examples of models that can be used in image rectification in accordance with this disclosure.
Figure 5D:
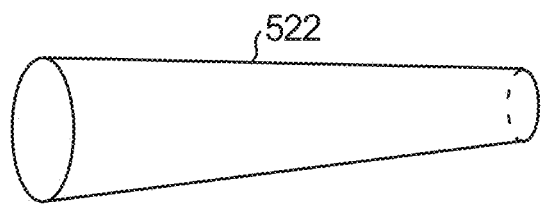
Figure 5E:
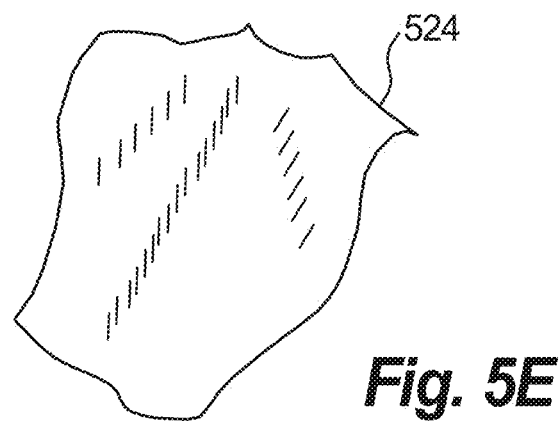

For example, with reference to FIG. 5C, the area of skin subject to the skin-prick test can be on a subject's forearm, wherein the model 516 includes an ellipsoidal-cross-section cylinder, and wherein the parameters of the model include the semi-minor axis 518 of the elliptical cross-section of the cylinder, the semi-major axis 520 of the elliptical cross-section of the cylinder, and orientation of the cylinder. It is also contemplated that the cylinder can include a cross-section that varies along the length thereof, as in model 522 of FIG. 5D, wherein the parameters include factors characterizing the change in area along the length of the cylinder. It is also contemplated that the area of skin subject to the skin-prick test can be on a subject's back, as in model 524 of FIG. 5E, wherein the model includes a parameterized abstraction of a back.

With reference to FIG. 1C, system 120 can be used for image correction for images of allergen skin reaction and includes an imaging device 122 including a projecting device 136, an output device 124, and a module 126 operatively connected to the imaging device 122 and the output device 124. The module 126 is configured to execute machine readable instructions to perform any embodiment or combination of embodiments of methods disclosed herein. The projecting device 136 can include a plurality of lasers mounted parallel to one another.

Figure 6A:
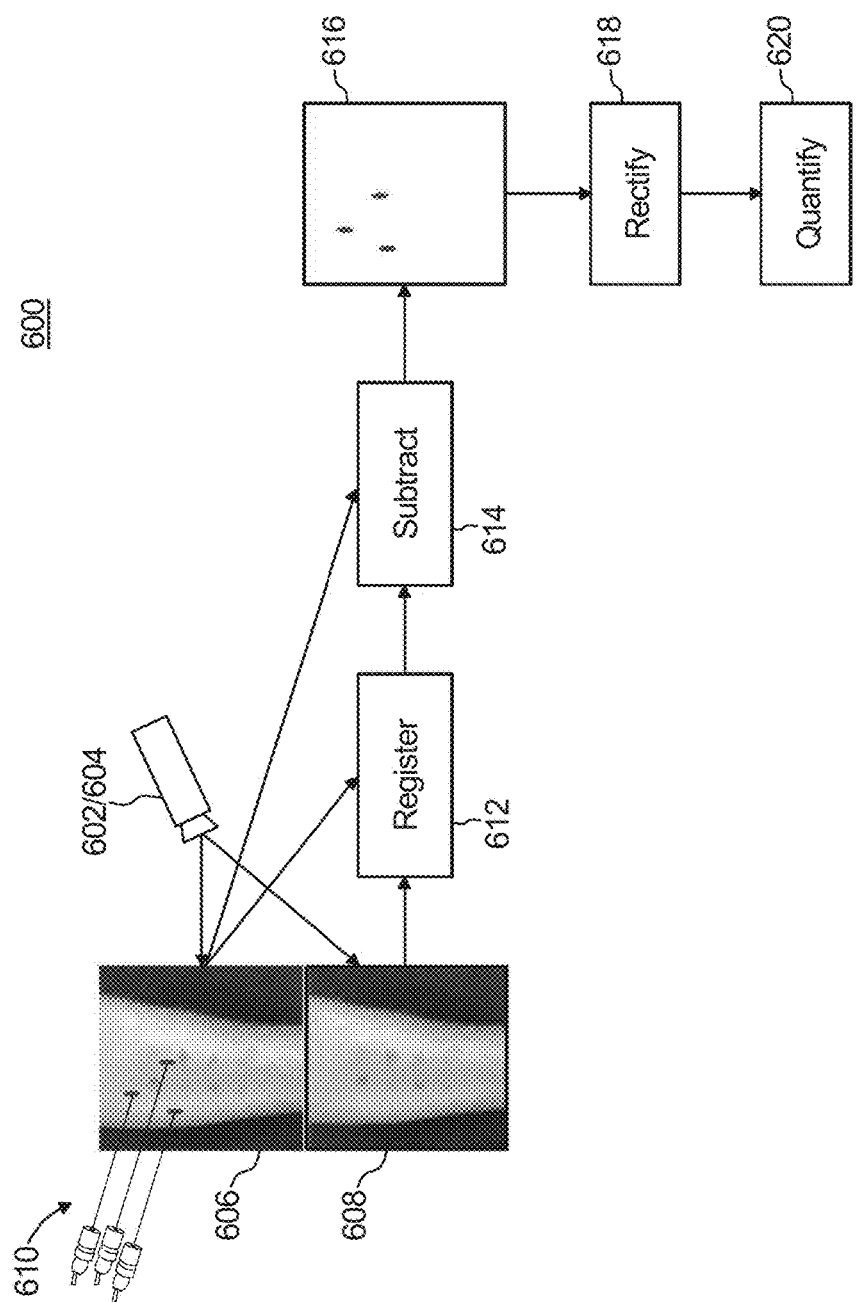
FIG. 6A is a schematic view of an exemplary embodiment of a method in accordance with this disclosure.

With reference now to FIG. 6A, a method 600 of image-based signal detection for correction for images of allergen skin reaction includes obtaining 602 a first image 606 of an area of skin that has been subjected to a skin prick-test and obtaining 604 a second image 608 of the area of skin. Obtaining 602/604 can include obtaining video images. Method 600 includes projecting 610 a metrology signal onto the area of skin during obtaining of at least one of the first and second images, e.g. image 606, so that the first and second images 606 and 608 differ with respect to presence of the metrology pattern. The method 600 includes registering 612 the first and second images 606 and 608 to form a registered pair of images. The registration may be achieved by feature detection, such as SIFT, SURF, ASIFT, other SIFT variants, a Harris Corner Detector, SUSAN, FAST, a Phase Correlation, a Normalized Cross-Correlation, GLOH, BRIEF, CenSure/STAR, ORB, or the like, and a random sample consensus (RANSAC) such as MSAC, MLESAC, Guided-MLESAC, PROSAC, KALMANSAC, and/or any other suitable technique. Method 600 includes performing a subtraction operation 614 on the registered pair of images to obtain an image 616 of the metrology pattern wherein the metrology pattern is substantially isolated from its surroundings. An image, e.g., image 608, of the area of skin can then be rectified 618 using the image 616 for quantification 620 of wheal and/or flare objects in the image rectified. The method includes outputting 620 data indicative of the quantified wheal and/or flare objects.

Rectifying the image of the area of skin can include correcting for camera pose to be as if the image were formed from an imaging device viewing the area of skin perpendicularly. Rectifying the image of the area of skin can include correcting for camera range to be as if the image were formed a predetermined distance from the area of skin. Rectifying an image can include rectification performed on an image that does not include the metrology pattern.

Obtaining 602/604 the first and second images 606 and 608 and projecting 610 the metrology signal can include obtaining one of the first and second images with the metrology signal projected, and obtaining the other of the first and second images with the metrology signal not projected. It is also contemplated that projecting 610 the metrology signal can include projecting the metrology signal with intensity that varies with time so the intensity of the metrology signal in the first and second images is different. For example, the metrology signal can be modulated sinusoidally at frequency f, and the images can be sampled by a video sensor at a frame rate of at least two times f, to make the metrology signal detectable. The method can include modeling the metrology signal and using the modeled metrology signal to subtract the metrology signal from one or more of the first and second images 606 and 608. Simply subtracting successive frames to isolate the metrology signal would tend to be insufficient and may introduce unwanted artifacts, e.g., since the sensor may move between successive frames relative to the subject. Thus image registration is performed before image subtracting.

Obtaining 602/604 the first and second images 606 and 608 can include obtaining both from a single imaging device. Obtaining 602/604 the first and second images 606 and 608 can include obtaining the images 606 and 608 on at least one of a sensor for visible light, a sensor for a non-visible portion of electromagnetic spectrum, or a three-dimensional sensor, and wherein projecting the metrology pattern includes projecting a metrology pattern detectible using the sensor.

Figure 6B:
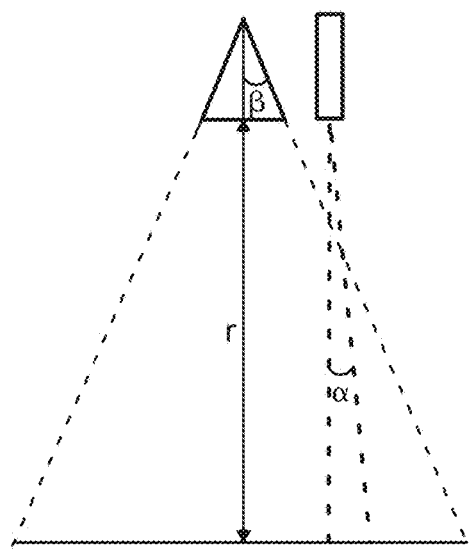
FIG. 6B is a schematic diagram showing a range finding technique using a single laser dot.
Figure 6B:
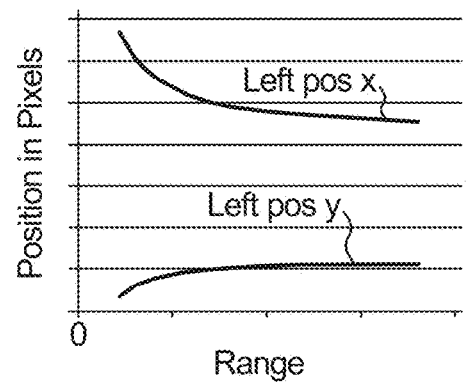

Projecting 610 a metrology signal onto the area of skin can include projecting a plurality of laser dots onto the area of the skin, e.g., three laser dots as in the example of FIG. 6A, but those skilled in the art will readily appreciate that any suitable number of laser dots can be used without departing from the scope of this disclosure. It is also contemplated that projecting 610 the metrology signal can include projecting a metrology signal having a single source including at least one of a predetermined shape that deforms under change in pose and distance, or is detected at a sensor separate from the projector. More generally, the projecting 610 may also allow determination of the three-dimensional shape of the skin area as with the use of depth sensing, e.g., projecting and determining a three-dimensional shape by a structured light measurement, a phase shift measurement, a time of flight measurement, or the like. It is further contemplated that projecting 610 the metrology signal can include projecting a metrology signal having a single laser dot, wherein rectifying an image includes range finding based on apparent position of the laser dot in the image of the metrology pattern wherein the metrology pattern is isolated from its surroundings. As shown in FIG. 6B, the apparent position of a laser dot (e.g., the width between left position x and left position y in the graph at the right in FIG. 6B), diminishes with distance over range r due to the difference in the angle defining the field of view (twice half-angle $\beta$ in FIG. 6B) and the angle $\alpha$ defining the divergence of the laser beam.

With reference now to FIG. 1C, system 120 can be used for image correction for images of allergen skin reaction and includes an imaging device 122 including a projecting device 136, an output device 124, and a module 126 operatively connected to the imaging device 122 and the output device 124. The module 126 is configured to execute machine readable instructions to perform any embodiment or combination of embodiments disclosed herein. The imaging device 122 can include at least one of a sensor 132 for visible light, a sensor 132 for a non-visible portion of electromagnetic spectrum, or a three-dimensional sensor 132. The projecting device 136 can be configured to project a metrology pattern detectible using the sensor 132.

Metrology signals as disclosed herein allow determination of the distance or determination of the pose and distance between a sensor and the object being imaged. Potential benefits of method 600 include that only one sensor is required, the metrology information does not confuse the object being detected and measured, and the image without metrology signals can be used to remove potentially confusing information from the image with metrology signals. While disclosed in the exemplary context of using optical sensors, e.g., cameras, and laser metrology devices, those skilled in the art will readily appreciate that any other suitable type of sensor or metrology device can be used without departing from the scope of this disclosure, including non-visible portions of the electromagnetic spectrum, three-dimensional sensors, and corresponding metrology devices.

As will be appreciated by one skilled in the art, aspects of the present embodiments may be embodied as a system, method or computer program product. Accordingly, aspects of the present embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." The system may be intended for stationary operation or may be in whole or in part a mobile device such as a mobile phone. Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), a digital video disk (DVD), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, e.g., module 126, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and/or block diagrams of methods, apparatus (systems) and computer program products according to embodiments of the embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in a flowchart and/or block diagram block or blocks.

The methods and systems of the present disclosure, as described above and shown in the drawings, provide for allergen skin reaction with superior properties compared to traditional techniques including better accuracy, consistency, convenience, and diagnostic significance. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A method of image-based signal detection for correction for images of allergen skin reaction comprising:
   obtaining a first image of an area of skin that has been subjected to a skin prick-test;
   obtaining a second image of the area of skin;
   projecting a metrology signal onto the area of skin during obtaining of at least one of the first and second images so that the first and second images differ with respect to presence of the metrology pattern, wherein projecting a metrology signal onto the area of skin includes projecting a plurality of laser dots onto the area of the skin;
   registering the first and second images to form a registered pair of images;
   performing a subtraction operation on the registered pair of images to obtain an image of the metrology pattern wherein the metrology pattern is isolated from its surroundings;
   rectifying an image of area of skin using the image of the metrology pattern isolated from its surroundings for quantification of wheal and/or flare objects in the image rectified; and
   outputting data indicative of the quantified wheal and/or flare objects.

2. A method as recited in claim 1, wherein rectifying the image of the area of skin includes correcting for camera pose to be as if the image were formed from an imaging device viewing the area of skin perpendicularly.

3. A method as recited in claim 1, wherein rectifying the image of the area of skin includes correcting for camera range to be as if the image were formed a predetermined distance from the area of skin.

4. A method as recited in claim 1, wherein obtaining the first and second images and projecting the metrology signal include:
   obtaining one of the first and second images with the metrology signal projected, and obtaining the other of the first and second images with the metrology signal not projected.

5. A method as recited in claim 4, further comprising:
   modeling the metrology signal and using the modeled metrology signal to subtract the metrology signal from at least one of the first and second images.

6. A method as recited in claim 1, wherein projecting the metrology signal includes projecting the metrology signal with intensity that varies with time so the intensity of the metrology signal in the first and second images is different.

7. A method as recited in claim 5, further comprising:
   modeling the metrology signal and using the modeled metrology signal to subtract the metrology signal from at least one of the first and second images.

8. A method as recited in claim 1, wherein obtaining the first and second images includes obtaining both from a single imaging device.

9. A method as recited in claim 1, wherein rectifying an image includes rectification performed on image that does not include the metrology pattern.

10. A method of image-based signal detection for correction for images of allergen skin reaction comprising:
   obtaining a first image of an area of skin that has been subjected to a skin prick-test;
   obtaining a second image of the area of skin;
   projecting a metrology signal onto the area of skin during obtaining of at least one of the first and second images so that the first and second images differ with respect to presence of the metrology pattern;
   registering the first and second images to form a registered pair of images;
   performing a subtraction operation on the registered pair of images to obtain an image of the metrology pattern wherein the metrology pattern is isolated from its surroundings;
   rectifying an image of area of skin using the image of the metrology pattern isolated from its surroundings for quantification of wheal and/or flare objects in the image rectified; and
outputting data indicative of the quantified wheal and/or flare objects, wherein projecting the metrology signal includes projecting a metrology signal having a single source including at least one of a predetermined shape that deforms under change in pose and distance.

11. A method of image-based signal detection for correction for images of allergen skin reaction comprising:
   obtaining a first image of an area of skin that has been subjected to a skin prick-test;
   obtaining a second image of the area of skin;
   projecting a metrology signal onto the area of skin during obtaining of at least one of the first and second images so that the first and second images differ with respect to presence of the metrology pattern;
   registering the first and second images to form a registered pair of images;
   performing a subtraction operation on the registered pair of images to obtain an image of the metrology pattern wherein the metrology pattern is isolated from its surroundings;
   rectifying an image of area of skin using the image of the metrology pattern isolated from its surroundings for quantification of wheal and/or flare objects in the image rectified; and
outputting data indicative of the quantified wheal and/or flare objects, wherein projecting the metrology signal includes projecting a metrology signal that is detected from a sensor separate from a projector projecting the metrology signal.

12. A method of image-based signal detection for correction for images of allergen skin reaction comprising:
   obtaining a first image of an area of skin that has been subjected to a skin prick-test;
   obtaining a second image of the area of skin;
   projecting a metrology signal onto the area of skin during obtaining of at least one of the first and second images so that the first and second images differ with respect to presence of the metrology pattern;
   registering the first and second images to form a registered pair of images;
   performing a subtraction operation on the registered pair of images to obtain an image of the metrology pattern wherein the metrology pattern is isolated from its surroundings;
   rectifying an image of area of skin using the image of the metrology pattern isolated from its surroundings for quantification of wheal and/or flare objects in the image rectified; and
outputting data indicative of the quantified wheal and/or flare objects, wherein projecting the metrology signal includes projecting a metrology signal having a single laser dot, wherein rectifying an image includes range finding based on apparent size of the laser dot in the image of the metrology pattern wherein the metrology pattern is isolated from its surroundings.

13. A method as recited in claim 1, wherein obtaining the first and second images includes obtaining the images on at least one of a sensor for visible light, a sensor for a non-visible portion of electromagnetic spectrum, or a three-dimensional sensor, and wherein projecting the metrology pattern includes projecting a metrology pattern detectable using the sensor.

14. A system for image correction for images of allergen skin reaction comprising:
   an imaging device including a projecting device;
   an output device;
   a module operatively connected to the imaging device and the output device, wherein the module is configured to execute machine readable instructions to:
   obtain a first image of an area of skin that has been subjected to a skin prick-test;
   obtain a second image of the area of skin;
   project a metrology signal onto the area of skin during obtaining of at least one of the first and second images so that the first and second images differ with respect to presence of the metrology pattern, wherein projecting a metrology signal onto the area of skin includes projecting a plurality of laser dots onto the area of the skin;
   register the first and second images to form a registered pair of images;
   perform a subtraction operation on the registered pair of images to obtain an image of the metrology pattern wherein the metrology pattern is isolated from its surroundings;
   rectify an image of area of skin using the image of the metrology pattern isolated from its surroundings for quantification of wheal and/or flare objects in the image rectified; and
   output data indicative of the quantified wheal and/or flare objects using the output device.

15. A system as recited in claim 14, wherein rectifying the image of the area of skin includes at least one of:
   correcting for camera pose to be as if the image were formed from an imaging device viewing the area of skin perpendicularly; or
   correcting for camera range to be as if the image were formed a predetermined distance from the area of skin.

16. A system as recited in claim 14, wherein the imaging device includes at least one of a sensor for visible light, a sensor for a non-visible portion of electromagnetic spectrum, or a three-dimensional sensor, and wherein the projecting device is configured to project a metrology pattern detectable using the sensor.

* * * * *